(12) United States Patent
Miyamoto et al.

(10) Patent No.: US 11,311,530 B2
(45) Date of Patent: *Apr. 26, 2022

(54) LEWY BODY DISEASE THERAPEUTIC AGENT CONTAINING PYRAZOLOQUINOLINE DERIVATIVE

(71) Applicant: Eisai R&D Management Co., Ltd., Tokyo (JP)

(72) Inventors: Mai Miyamoto, Tsukuba (JP); Yukio Ishikawa, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/611,374

(22) PCT Filed: May 30, 2018

(86) PCT No.: PCT/JP2018/020650
§ 371 (c)(1),
(2) Date: Nov. 6, 2019

(87) PCT Pub. No.: WO2018/221551
PCT Pub. Date: Dec. 6, 2018

(65) Prior Publication Data
US 2020/0155541 A1    May 21, 2020

Related U.S. Application Data

(60) Provisional application No. 62/513,727, filed on Jun. 1, 2017.

(51) Int. Cl.
*A61K 31/4745* (2006.01)
*A61P 25/28* (2006.01)

(52) U.S. Cl.
CPC .......... *A61K 31/4745* (2013.01); *A61P 25/28* (2018.01)

(58) Field of Classification Search
CPC .............................. A61K 31/4745; A61P 25/28
USPC ......................................................... 514/293
See application file for complete search history.

(56) References Cited

U.S. PATENT DOCUMENTS

| | | | |
|---|---|---|---|
| 8,563,565 B2 | 10/2013 | Norimine et al. | |
| 2006/0035920 A1 | 2/2006 | Boyle et al. | |
| 2009/0131467 A1 | 5/2009 | Kanazawa et al. | |
| 2010/0048556 A1 | 2/2010 | Okada et al. | |
| 2010/0210839 A1 | 8/2010 | Böss et al. | |
| 2011/0082137 A1 | 4/2011 | Giovannini et al. | |
| 2011/0131467 A1 | 6/2011 | Weathers | |
| 2011/0184000 A1 | 7/2011 | Giovannini et al. | |
| 2011/0319385 A1 | 12/2011 | Kaizawa et al. | |
| 2013/0085134 A1 | 4/2013 | Kaizawa et al. | |
| 2013/0143907 A1 | 6/2013 | Norimine et al. | |
| 2013/0225553 A1 | 8/2013 | Kaizawa et al. | |
| 2013/0225572 A1 | 8/2013 | Okada et al. | |
| 2013/0296352 A1 | 11/2013 | Norinine et al. | |
| 2016/0046623 A1 | 2/2016 | Ozaki | |
| 2020/0078306 A1 | 3/2020 | Schuck et al. | |
| 2020/0129488 A1 | 4/2020 | Miyamoto et al. | |
| 2020/0129501 A1 | 4/2020 | Miyamoto et al. | |

FOREIGN PATENT DOCUMENTS

| | | |
|---|---|---|
| AU | 2008249750 | 11/2008 |
| CA | 2754457 | 9/2010 |
| CN | 101553491 | 10/2009 |
| CN | 101983199 | 3/2011 |
| CN | 102365285 | 8/2014 |
| EA | 200500322 | 8/2005 |
| EP | 0934273 | 8/1999 |
| EP | 1925617 | 5/2008 |
| EP | 2103613 | 9/2009 |
| EP | 2152712 | 2/2010 |
| EP | 2769980 | 8/2014 |
| EP | 2982675 | 2/2016 |
| JP | H5-132484 | 5/1993 |
| JP | H9-506634 | 6/1997 |
| JP | 2006-045118 | 2/2006 |
| JP | 2011-516454 | 5/2011 |
| JP | 2012-515761 | 7/2012 |
| JP | 2013-067595 | 4/2013 |
| JP | 5546693 | 5/2014 |
| MX | 2014/003800 | 7/2014 |
| RU | 2383546 | 8/2006 |
| RU | 2426734 | 8/2011 |
| RU | 2605096 | 11/2015 |
| RU | 2655171 | 5/2017 |

(Continued)

OTHER PUBLICATIONS

Donepezil for Dimentia with Lewy Bodies; A randomized, Placebo-controlled trial. (Year: 2012).*

(Continued)

*Primary Examiner* — Niloofar Rahmani
(74) *Attorney, Agent, or Firm* — Fish & Richardson P.C.

(57) ABSTRACT

Provided is a therapeutic agent for Lewy body disease comprising (S)-7-(2-methoxy-3,5-dimethylpyridin-4-yl)-1-(tetrahydrofuran-3-yl)-1H-pyrazolo[4,3-c]quinolin-4(5H)-one represented by formula (I)

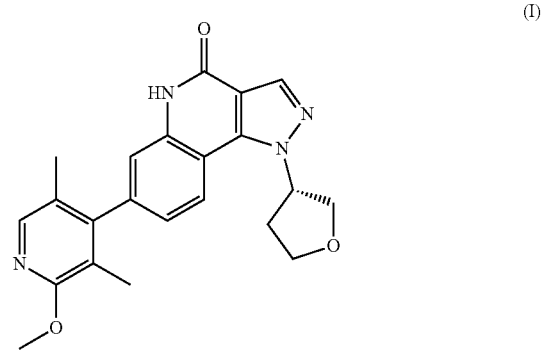

or a pharmaceutically acceptable salt thereof.

1 Claim, No Drawings

(56) References Cited

FOREIGN PATENT DOCUMENTS

| WO | WO 95/32205 | 11/1995 |
|---|---|---|
| WO | WO 1998/016512 | 4/1998 |
| WO | WO 2003/037899 | 5/2003 |
| WO | WO 2007/032466 | 3/2007 |
| WO | WO 2008/072778 | 6/2008 |
| WO | WO 2008/072779 | 6/2008 |
| WO | WO 2008/139293 | 11/2008 |
| WO | WO 2009/121919 | 10/2009 |
| WO | WO 2010/026214 | 3/2010 |
| WO | WO 2010/084438 | 7/2010 |
| WO | WO 2010/101230 | 9/2010 |
| WO | WO 2012/020022 | 2/2012 |
| WO | WO 2012/033144 | 3/2012 |
| WO | WO 2012/110440 | 8/2012 |
| WO | WO 2013/045400 | 4/2013 |
| WO | WO 2013/051639 | 4/2013 |
| WO | WO 2014/163146 | 10/2014 |
| WO | WO 2014/163147 | 10/2014 |

OTHER PUBLICATIONS

Abstract Joshua Vardigan et al., The selective Phosphodiesterase 9 (PDE9) Inhibitor PF-04447943 attenuates a scopolamine-induced Deficit in a novel Rodent Attention task. (Year: 2011).*
Chiu et al., "Donepezil in the one-year treatment of dementia with Lewy bodies and Alzheimer's disease," Journal of Neurological Sciences, 2017, 381:p322, XP085294732, 1 page.
Magierski et al., "1.206—Donepezil versus rivastigmine tolerability study in dementia with Lewy bodies and Alzheimer's disease," Parkinsonism and Related Disorders, Elsevier Science, Oxford, GB, 2007, 13:S62, XP022635787, 1 page.
Notice of Allowance in U.S. Appl. No. 16/607,402, dated Jan. 13, 2021, 23 pages.
Notice of Allowance in U.S. Appl. No. 16/607,459, dated Jan. 14, 2021, 23 pages.
Notice of Allowance in U.S. Appl. No. 16/607,459, dated Feb. 3, 2021, 4 pages.
Office Action in Egyptian Patent Application No. PCT529/2014, dated Dec. 7, 2020, 12 pages (with English Translation).
Office Action in U.S. Appl. No. 16/609,514, dated Dec. 9, 2020, 24 pages.
Official Notification in U.S. Appl. No. 16/607,402, dated Mar. 9, 2021, 2 pages.
Official Notification in U.S. Appl. No. 16/607,459, dated Mar. 2, 2021, 2 pages.
Search Report in European Patent Application No. 18808870.2, dated Feb. 17, 2021, 4 pages.
Search Report in European Patent Application No. 18809656.4, dated Jan. 22, 2021, 7 pages.
Search Report in European Patent Application No. 18810578.7, dated Jan. 20, 2021, 6 pages.
Submission Document in Egyptian Patent Application No. PCT529/2014, dated Mar. 4, 2021, 12 pages (with English Translation).
Submission Document in U.S. Appl. No. 16/607,402, dated Feb. 23, 2021, 17 pages.
Submission Document in U.S. Appl. No. 16/607,459, dated Feb. 23, 2021, 18 pages.
Ando et al., "Preclinical Characterization of E2027, A Novel Phosphodiesterase 9 Inhibitor," Alzheimer's & Dementia: The Journal of the Alzheimer's Association, Jul. 2017, 13(7):XP085217616, 1 page.
Office Action in Mexican Patent Application No. MX/a/2019/013198, dated Oct. 5, 2020, 7 pages (with English Translation).
Search Report in European Patent Application No. 18810202.4, dated Nov. 23, 2020, 9 pages.
Submission Document in Israeli Patent Application No. 270318, dated Nov. 16, 2020, 55 pages (with English Translation).
Submission Document in Israeli Patent Application No. 270357, dated Dec. 7, 2020, 5 pages (with English Translation).
Submission Document in Israeli Patent Application No. 270394, dated Nov. 15, 2020, 40 pages (with English Translation).
Submission Document in Israeli Patent Application No. 270395, dated Nov. 17, 2020, 35 pages (with English Translation).
Submission Document in Mexican Patent Application No. MX/a/2019/013198, dated Dec. 2, 2020, 12 pages (with English Translation).
Submission Document in U.S. Appl. No. 16/609,514, dated Nov. 25, 2020, 11 pages.
[No Author Listed], "Eisai Scientific Meeting 2019," Presentation, Eisai Co., Ltd., Apr. 23, 2019, 137 pages.
Ando et al., "Effects of repeated administration of E2027, a novel phosphodiesterase-9 inhibitor, on cyclic GMP levels in rat cerebrospinal fluid," Poster presented at Alzheimer's Association International Conference (AAIC), Chicago, IL, Jul. 22-26, 2018, P3-062, 1 page.
Ando et al., "Preclinical characterization of E2027, a novel phosphodiesterase (PDE) 9 inhibitor," Poster presented at Alzheimer's Association International Conference (AAIC), Jul. 16-20, 2017, P3-043, 1 page.
Goto et al., "Effect of E2027, a Novel Phosphodiesterase-9 Inhibitor, on Cognitive Function and Hippocampal Cyclic GMP in Tg2576 Mouse Model of Alzheimer's Disease," Poster presented at 15th International Conference on Alzheimer's & Parkinson Disease (AD/PD), Virtual Conference, Mar. 9-14, 2021, P153, 1 page.
Lai et al., "Phase 1 Investigation into the Safety, Tolerability, Pharmacokinetics (PK) and Pharmacodynamics (PD) of E2027, a Selective Phosphodiesterase-9 (PDE9) Inhibitor," Presentation slides presented at Alzheimer's Association International Conference (AAIC), Jul. 16-20, 2017, pp. 1-10.
Landry et al., "Concentration Response Modeling of ECG Data for E2027 to Inform Dose Selection for Phase 2 Dementia in Lewy Body Study," Poster presented at 14th International Conference on Alzheimer's & Parkinson's Diseases, (AD/PD 2019), Lisbon, Portugal, Mar. 26-31, 2019, 1 page.
Landry et al., "E2027, a novel phosphodiesterase-9 (PDE9) inhibitor in development for treatment of dementia with Lewy bodies (DLB), showed no clinically significant drug interaction with diltiazem," Poster presented at Alzheimer's Association International Conference (AAIC), Chicago, IL, Jul. 22-26, 2018, P1-055, 1 page.
Landry et al., "Phase 1 Multiple Ascending Dose (MAD) Study of Phosphodiesterase-9 Inhibitor E2027: Confirmation of Target Engagement and Selection of Phase 2 Dose in Dementia with Lewy Bodies," Presentation slides presented at Alzheimer's Association International Conference (AAIC), Jul. 22-26, 2018, pp. 1-10.
Notice of Allowance in Australian Patent Application No. 2014250392, dated Feb. 14, 2018, 3 pages.
Notice of Allowance in Canadian Patent Application No. 2861795, dated Sep. 7, 2018, 1 page (with English Translation).
Notice of Allowance in Canadian Patent Application No. 2907971, dated Sep. 1, 2020, 1 page (with English Translation).
Notice of Allowance in Chinese Patent Application No. 201280046653.2, dated Jun. 23, 2015, 4 pages (with English Translation).
Notice of Allowance in Chinese Patent Application No. 201480017423.2, dated Mar. 20, 2017, 4 pages (with English Translation).
Notice of Allowance in Colombian Patent Application No. 14-059034, dated Aug. 18, 2015, 6 pages (with English Translation).
Notice of Allowance in European Patent Application No. 12837953.4, dated Aug. 26, 2015, 156 pages.
Notice of Allowance in European Patent Application No. 14780139.3, dated Apr. 6, 2017, 62 pages.
Notice of Allowance in Indonesian Patent Application No. P00201401905, dated Mar. 25, 2019, 5 pages (with English Translation).
Notice of Allowance in Korean Patent Application No. 10-2014-7008769, dated Dec. 3, 2018, 4 pages (with English Translation).
Notice of Allowance in Korean Patent Application No. 10-2015-7026005, dated May 1, 2019, 6 pages (with English Translation).
Notice of Allowance in Mexican Patent Application No. MX/a/2014/003800, dated Jun. 22, 2018, 4 pages (with English Translation).

(56) References Cited

OTHER PUBLICATIONS

Notice of Allowance in Mexican Patent Application No. MX/a/2015/013620, dated Sep. 18, 2018, 5 pages (with English Translation).
Notice of Allowance in Pakistani Patent Application No. 458/2016, dated Mar. 19, 2020, 1 page.
Notice of Allowance in Pakistani Patent Application No. 672/2012, dated Mar. 19, 2020, 1 page.
Notice of Allowance in Singaporean Patent Application No. 11201507897S, dated Oct. 27, 2017, 5 pages.
Notice of Allowance in Thai Patent Application No. 1401001864, dated Sep. 26, 2019, 2 pages (with English Translation).
Notice of Allowance in U.S. Appl. No. 14/778,695, dated Nov. 4, 2016, 9 pages.
Office Action in Canadian Patent Application No. 2861795, dated May 30, 2018, 3 pages.
Office Action in Canadian Patent Application No. 2907971, dated Apr. 28, 2020, 5 pages.
Office Action in Indian Patent Application No. 2463/CHENP/2014, dated Jun. 11, 2018, 6 pages (with English Translation).
Office Action in Indian Patent Application No. 5808/CHENP/2015, dated Oct. 26, 2018, 5 pages (with English Translation).
Office Action in Indian Patent Application No. 5808/CHENP/2015, dated May 28, 2019, 2 pages (with English Translation).
Office Action in Indonesian Patent Application No. P00201401905, dated Nov. 26, 2018, 5 pages (with English Translation).
Office Action in Israeli Patent Application No. 241796, dated Feb. 14, 2018, 8 pages (with English Translation).
Office Action in Korean Patent Application No. 10-2014-7008769, dated Sep. 3, 2018, 8 pages (with English Translation).
Office Action in Korean Patent Application No. 10-2015-7026005, dated Jan. 2, 2019, 10 pages (with English Translation).
Office Action in Malaysian Patent Application No. PI2014700702, dated Jun. 29, 2018, 3 pages.
Office Action in Mexican Patent Application No. MX/a/2014/003800, dated Jan. 15, 2018, 9 pages (with English Translation).
Office Action in Mexican Patent Application No. MX/a/2015/013620, dated May 22, 2018, 13 pages (with English Translation).
Office Action in Pakistani Patent Application No. 458/2016, dated Apr. 6, 2018, 2 pages.
Schuck et al., "Population pharmacokinetic-pharmacodynamic (PPK/PD) modeling of E2027, a selective phosphodiesterase-9 (PDE9) inhibitor, following single ascending oral doses in healthy volunteers," Poster presented at Alzheimer's Association International Conference (AAIC), Jul. 16-20, 2017, P1-056, 1 page.
Submission Document in Canadian Patent Application No. 2861795, dated Jul. 17, 2018, 12 pages.
Submission Document in Canadian Patent Application No. 2907971, dated Jun. 26, 2020, 12 pages.
Submission Document in Indian Patent Application No. 2463/CHENP/2014, dated Nov. 30, 2018, 10 pages.
Submission Document in Indian Patent Application No. 5808/CHENP/2015, dated Jan. 16, 2019, 6 pages.
Submission Document in Indian Patent Application No. 5808/CHENP/2015, dated Jul. 2, 2019, 88 pages.
Submission Document in Indonesian Patent Application No. P00201401905, dated Feb. 22, 2019, 7 pages (with English Translation).
Submission Document in Israeli Patent Application No. 241796, dated Jun. 3, 2018, 3 pages (with English Translation).
Submission Document in Korean Patent Application No. 10-2014-7008769, dated Oct. 1, 2018, 11 pages (with English Translation).
Submission Document in Korean Patent Application No. 10-2015-7026005, dated Feb. 14, 2019, 23 pages (with English Translation).
Submission Document in Mexican Patent Application No. MX/a/2014/003800, dated Feb. 16, 2018, 4 pages (with English Translation).
Submission Document in Mexican Patent Application No. MX/a/2015/013620, dated Jun. 25, 2018, 8 pages (with English Translation).
Submission Document in Pakistani Patent Application No. 458/2016, dated Jul. 2, 2018, 3 pages.
Submission Document in Pakistani Patent Application No. 458/2016, dated May 29, 2020, 8 pages.
Submission Document in U.S. Appl. No. 16/609,514, dated Mar. 9, 2021, 13 pages.
Office Action in Israeli Patent Application No. 270318, dated Aug. 23, 2020, 5 pages (with English Translation).
Office Action in Israeli Patent Application No. 270357, dated Aug. 23, 2020, 5 pages (with English Translation).
Office Action in Israeli Patent Application No. 270394, dated Aug. 23, 2020, 5 pages (with English Translation).
Office Action in Israeli Patent Application No. 270395, dated Aug. 23, 2020, 5 pages (with English Translation).
Notice of Allowance in Russian Patent Application No. 2015140619, dated Apr. 20, 2021, 12 pages (with English Translation).
Notice of Allowance in Vietnamese Patent Application No. 1-2014-01049, dated Jul. 31, 2017, 2 pages (with English Translation).
Office Action in Argentine Patent Application No. P120103702, dated Aug. 16, 2019, 4 pages (with English Translation).
Office Action in Brazilian Patent Application No. BR112014007912-9, dated Jul. 2, 2019, 10 pages (with English Translation).
Office Action in Brazilian Patent Application No. BR112015024393-2, dated Oct. 22, 2019, 10 pages (with English Translation).
Office Action in Mexican Patent Application No. MX/a/2019/013198, dated Mar. 18, 2021, 8 pages (with English Translation).
Office Action in Peruvian Patent Application No. 000408-2014, dated Mar. 12, 2018, 13 pages (with English Translation).
Office Action in Russian Patent Application No. 2015140619, dated Mar. 26, 2018, 12 pages (with English Translation).
Office Action in Vietnamese Patent Application No. 1-2014-01049, dated May 15, 2014, 2 pages (with English Translation).
Office Action in Vietnamese Patent Application No. 1-2014-01049, dated May 16, 2017, 2 pages (with English Translation).
Submission Document in Argentine Patent Application No. P120103702, dated Oct. 24, 2019, 10 pages (with English Translation).
Submission Document in Brazilian Patent Application No. BR112014007912-9, dated Aug. 26, 2019, 12 pages (with English Translation).
Submission Document in Brazilian Patent Application No. BR112015024393-2, dated Jan. 17, 2020, 18 pages (with English Translation).
Submission Document in Peruvian Patent Application No. 000408-2014, dated Apr. 10, 2018, 14 pages (with English Translation).
Submission Document in Russian Patent Application No. 2015140619, dated Apr. 10, 2018, 12 pages (with English Translation).
Submission Document in Vietnamese Patent Application No. 1-2014-01049, dated Jun. 12, 2014, 19 pages (with English Translation).
Submission Document in Vietnamese Patent Application No. 1-2014-01049, dated Jun. 8, 2017, 11 pages (with English Translation).
Office Action in U.S. Appl. No. 16/609,514, dated Oct. 2, 2020, 9 pages.
Bergman et al., "Successful Use of Donepezil for the Treatment of Psychotic Symptoms in Patients With Parkinson's Disease," Clinical Neuropharmacology, Mar.-Apr. 2002, 25(2):107-110.
Bonkale et al., "Reduced nitric oxide responsive soluble guanylyl cyclase activity in the superior temporal cortex of patients with Alzheimer's disease," Neuroscience Letters, 1995, 187:5-8.
Bourke et al., "Possible association between donepezil and worsening Parkinson's disease," The Annals of Pharmacotherapy, 1998, 32:610-611.
Brandon and Rotella, "Potential CNS-14 Applications for Phosphodiesterase Enzyme Inhibitors," Annual Reports in Medicinal Chemistry, 2007, 42:3-12.
Chinese Observations in Application No. 201480016592.4, dated Nov. 4, 2015, 2 pages, (with English Translation).
Cummings et al., "Pimavanserin for patients with Parkinson's disease psychosis: a randomised, placebo-controlled phase 3 trial," The Lancet, Feb. 2014, 383(9916):533-540.
Domek-Lopacińska et al., "Cyclic GMP Metabolism and its role in brain physiology," Journal of Physiology and Pharmacology, 2005, 56:15-34.

(56) References Cited

OTHER PUBLICATIONS

Dubois et al., "Donepezil in Parkinson's Disease Dementia: A Randomized Double-Blind Efficacy and Safety Study," Movement Disorders, Sep. 2012, 27(10):1230-1238.
Eisai Co. Ltd. [Online], "Press Conference; Materials in reporter meeting," Mar. 2017, [Retrieved on Jul. 3, 2018], Retrieved from: URL<https://www.eisai.co.jp/ir/library/presentations/pdf/4523_170309>, 96 pages (with English Translation).
European Response to Office Action in Application No. 14780073.4, dated May 11, 2016, 5 pages.
European Response to Office Action in Application No. 14780139.3, dated May 10, 2016, 4 pages.
European Search Report in Application No. 14780073.4, dated Jul. 28, 2016, 4 pages.
European Search Report in Application No. 14780139.3, dated Jul. 13, 2016, 5 pages.
Extended European Search Report in European Application No. 12837953.4, dated Jan. 27, 2015, 10 pages.
Fisher et al., "Isolation and Characterization of PDE9A, a Novel Human cGMP-specific Phosphodiesterase," The Journal of Biological Chemistry, 1998, 273(25): 15559-15564.
Gauthier et al., "Efficacy of Donepezil on Behavioral Symptoms in Patients With Moderate to Severe Alzheimer's Disease," International Psychogeriatrics, 2002, 14(4):389-404.
Grossberg et al., "Memantine Therapy of Behavioral Symptoms in Commumty-Dwelling Patients with Moderate to Severe Alzheimer's Disease," Dementia and Geriatric Cognitive Disorders, 2009, 27:164-172.
Holmes et al., "The efficacy of donepezil in the treatment of neuropsychiatric symptoms in Alzheimer disease," Neurology, 2004, 63:214-219.
Homma et al., "Clinical Efficacy and Safety of Donepezil on Cognitive and Global Function in Patients with Alzheimer's Disease," Dementia and Geriatric Cognitive Disorders, 2000, 11:299-313.
Homma et al., "Donepezil Treatment of Patients with Severe Alzheimer's Disease in a Japanese Population: Results from a 42-Week, Double-Blind, Placebo-Controlled, Randomized Trial," Dementia and Geriatric Cognitive Disorders, Apr. 2008, 25:399-407.
Horita et al., "Effects of the adenosine A2A antagonist istradefylline on cognitive performance in rats with a 6-OHDA lesion in prefrontal cortex," Psychopharmacology, Dec. 2013, 230(3):345-352.
Howard et al., "Donepezil and Memantine for Moderate-to-Severe Alzheimer's Disease," The New England Journal of Medicine, 2012, 366:893-903.
Hutson et al., "The selective phosphodiesterase 9 (PDE9) inhibitor PF-04447943 (6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one) enhances synaptic plasticity and cognitive function in rodents," Neuropharmacology, Sep. 2011, 61(4):665-676.
International Preliminary Report on Patentability in International Application No. PCT/JP2012/075748, dated Apr. 17, 2014, 10 pages.
International Preliminary Report on Patentability in International Application No. PCT/JP2014/059852, dated Oct. 15, 2015, 8 pages.
International Preliminary Report on Patentability in International Application No. PCT/JP2014/059853, dated Oct. 15, 2015, 7 pages.
International Preliminary Report on Patentability in International Application No. PCT/JP2018/020638, dated Dec. 12, 2019, 7 pages.
International Preliminary Report on Patentability in International Application No. PCT/JP2018/020649, dated Dec. 12, 2019, 6 pages.
International Preliminary Report on Patentability in International Application No. PCT/JP2018/020650, dated Dec. 12, 2019, 8 pages.
International Search Report and Written Opinion in International Application No. PCT/JP2018/020643, dated Aug. 21, 2018, 4 pages.
International Search Report in International Application No. PCT/JP2012/075748, dated Nov. 20, 2012, 8 pages (with English Translation).
International Search Report in International Application No. PCT/JP2018/020638, dated Aug. 21, 2018, 4 pages (with English Translation).
International Search Report in International Application No. PCT/JP2018/020649, dated Aug. 21, 2018, 3 pages (with English Translation).
International Search Report in International Application No. PCT/JP2018/020650, dated Aug. 21, 2018, 4 pages (with English Translation).
Japanese Society of Neurology [Online], "Dementia with Lewy bodies (included Parkinson's disease)," Chapter 7, Online Dementia disease treatment guidelines, 2010, [Retrieved on Jul. 3, 2018], Retrieved from: URL<http://www.neurology-jp.org.guidelinem/degl/sinkei_degl_2010_08.pdf>, pp. 300-302 (with Partial Translation).
Kleiman et al., "Phosphodiesterase 9A Regulates Central cGMP and Modulates Responses to Cholinergic and Monoaminergic Perturbation in Vivo," J Pharmacol. Exp. Thera., Feb. 9, 2012, 341(2):396-409.
Lopez et al., "Long-term effects of the concomitant use of memantine with cholinesterase inhibition in Alzheimer disease," J Neurol Neurosurg Psychiatry, 2009, 80(6):600-607.
Mckeith et al., "Diagnosis and management of dementia with Lewy bodies: third report of the DLB Consortium," Neurology, Dec. 2005, 65(12): 1863-1872.
McKeith et al., "Efficacy of rivastigmine in dementia with Lewy bodies: a randomised, double-blind, placebo-controlled international study," The Lancet, Dec. 2000, 356(9247):2031-2036.
Mecocci et al., "Effects of memantine on cognition in patients with moderate to severe Alzheimer's disease: post-hoc analyses of ADAS-cog and SIB total and single-item scores from six randomized, double-blind, placebo-controlled studies," International Journal of Geriatric Psychiatry, 2009, 24:532-538.
Mori et al., "Donepezil for Dementia with Lewy Bodies: A Randomized, Placebo-Controlled Trial," Annals of Neurology, 2012, 72:41-52.
Neurology-jp.org [online], "Dementia with Lewy bodies included Parkinson's disease," 2010, [Retrieved on Jan. 16, 2020], retrieved from: URL<http://www.neurology-jp.org/guidelinem/degl/sinkei_degl_2010_08.pdf>, pp. 300-302 (with English Translation).
Notice of Allowance in Australian Patent Application No. 2012319549, dated Jul. 19, 2016, 3 pages.
Notice of Allowance in Israeli Patent Application No. 231650, dated Feb. 10, 2016, 5 pages, (with English Translation).
Notice of Allowance in Japanese Patent Application No. P2013-537544, dated Apr. 30, 2014, 6 pages, (with English Translation).
Notice of Allowance in Russian Patent Application No. 2014112931, dated Aug. 22, 2016, 19 pages, (with English translation).
Notice of Allowance in Singaporean Patent Application No. 11201400717Q, dated May 26, 2016, 4 pages.
Notice of Allowance in South African Patent Application No. 2014/02439, dated Jan. 21, 2015, 3 pages.
Notice of Allowance in Taiwanese Patent Application No. 101136747, dated Aug. 17, 2016, 5 pages, (with English Translation).
Notice of Allowance in U.S. Appl. No. 13/644,745, dated Jun. 10, 2013, 13 pages.
Office Action in Australian Patent Application No. 2012319549, dated Jun. 1, 2016, 7 pages.
Office Action in Chilean Patent Application No. 2014-00821, dated Oct. 29, 2015, 11 pages, (with English Translation).
Office Action in Chinese Patent Application No. 201280046653.2, dated Feb. 28, 2015, 10 pages, (with English Translation).
Office Action in Chinese Patent Application No. 201480016592.4, dated May 12, 2016, 12 pages, (with English Translation).
Office Action in Chinese Patent Application No. 201480016592.4, dated Oct. 16, 2015, 2 pages, (with English Translation).
Office Action in Chinese Patent Application No. 201480017423.2, dated Mar. 1, 2016, 10 pages, (with English Translation).
Office Action in Colombian Patent Application No. 14-059034, dated Mar. 10, 2015, 13 pages, (with English translation).
Office Action in Filipino Patent Application No. 1-2014-500580, dated Jun. 17, 2016, 3 pages.
Office Action in Golf Cooperation Council Patent Application No. GC2012-22447, dated Apr. 21, 2016, 4 pages.

(56) References Cited

OTHER PUBLICATIONS

Office Action in Israeli Patent Application No. 231650, dated Jul. 16, 2014, 4 pages, (with English Translation).
Office Action in Israeli Patent Application No. 241695, dated Jan. 24, 2016, 5 pages, (with English Translation).
Office Action in Israeli Patent Application No. 241796, dated Jan. 24, 2016, 5 pages, (with English Translation).
Office Action in Japanese Patent Application No. P2014-538559, dated Sep. 30, 2014, 4 pages, (with English Translation).
Office Action in New Zealand Patent Application No. 622594, dated Feb. 4, 2015, 2 pages.
Office Action in Pakistani Patent Application No. 672/2012, dated Feb. 14, 2013, 8 pages.
Office Action in Taiwanese Patent Application No. 101136747, dated Apr. 22, 2016, 5 pages, (with English Translation).
Office Action in U.S. Appl. No. 13/644,745, dated Mar. 26, 2013, 8 pages.
Office Action in Vietnamese Patent Application No. 1-2015-03459, dated Nov. 25, 2015, 2 pages, (with English Translation).
"PF-04447943: A Phase 2 Controlled Clinical Trial of a Selective PDE9A Inhibitor in Alzheimer's Disease, Apr. 6, 2005," Abstract of Alzheimer's Association International Conference (AAIC) 2011, Jul. 16-21, 2011; Pair, France, 1 page.
Perry et al., "Neocortical cholinergic activities differentiate Lewy body dementia from classical Alzheimer's disease," Neuroreport, Mar. 1994, 5(7):747-749.
Raskind et al., "Galantamine in AD: A 6-month randomized, placebo-controlled trial with a 6-month extension," Neurology, 2000, 54:2261-2268.
Response filed in Chilean Office Action in Application No. 2014-00821, dated Aug. 19, 2015, 26 pages, (with English Translation).
Response filed in Chilean Office Action in Application No. 2014-00821, dated Dec. 16, 2015, 6 pages, (with English Translation).
Response to Examination Report in Australian Patent Application No. 2012319549, dated Jul. 8, 2016, 6 pages.
Response to Extended European Search Report in European Patent Application No. 12837953.4, dated May 15, 2015, 22 pages.
Response to Office Action filed in Chinese Patent Application No. 201280046653.2, dated Apr. 28, 2015, 16 pages, (with Enghsh Translation).
Response to Office Action filed in Colombian Patent Application No. 14-059034, dated Jul. 16, 2015, 23 pages, (with English translation).
Response to Office Action in Israeli Patent Application No. 231650, dated Nov. 6, 2014, 8 pages, (with English Translation).
Response to Office Action in Israeli Patent Application No. 241695, dated May 23, 2016, 4 pages (with English Translation).
Response to Office Action in Israeli Patent Application No. 241796, dated May 23, 2016, 4 pages, (with English Translation).
Response to Office Action in New Zealand Patent Application No. 622594, dated May 22, 2015, 16 pages.
Response to Office Action in Russian Patent Application No. 2014112931, dated Jul. 26, 2016, 23 pages, (with English Translation).
Response to Office Action in Vietnamese Patent Application No. 1-2015-03459, dated Dec. 17, 2015, 21 pages, (with English translation).
Sambeth et al., "Cholinergic drugs affect novel object recognition in rats: Relation with hippocampal EEG?," European Journal of Pharmacology, Oct. 2007, 572(2-3): 151-159.
Shimada et al., "Mapping of brain acetylcholinesterase alterations in Lewy body disease by PET," Neurology, Jul. 2009, 73(4):273-278.
Singapore Request to Amend Application Before Grant in Application No. 11201400717Q, dated Feb. 12, 2016, 9 pages.
Snyder et al., "Reversal of scopolamine-induced deficits with a single dose of donepezil, an acetylcholinesterase inhibitor," Alzheimer's & Dementia, Oct. 2005,1(2): 126-135.
Submission Document in Filipino Patent Application No. 1-2014-500580, dated Aug. 30, 2016, 3 pages.
Submission Document in Filipino Patent Application No. 1-2014-500580, dated Jul. 21, 2016, 5 pages.
Submission Document in Gulf Cooperation Council Patent Application No. GC2012-22447, dated Jul. 18, 2016, 4 pages, (with English Translation).
Submission Document in Malaysian Patent Application No. PI2014700702, dated Sep. 28, 2016, 12 pages, (with English Translation).
Submission Document in Pakistani Patent Application No. 672/2012, dated Jul. 28, 2016, 17 pages, (with English Translation).
Submission Document in Taiwanese Patent Application No. 101136747, dated Jul. 21, 2016, 15 pages, (with English Translation).
Submission Document in Thai Patent Application No. 1401001864, dated Feb. 15, 2016, 352 pages, (with English Translation).
Submission Documents in Chinese Patent Application No. 2014/80017423.2, dated Jul. 4, 2016, 6 pages, (with English Translation).
Takano et al., "Oral Absorption of Poorly Water-Soluble Drugs: Computer Simulation of Fraction Absorbed in Humans From a Miniscale Dissolution Test," PharmRes, Jun. 2006, 23(6):1144-1156.
Tiraboschi et al., "Cholinergic dysfunction in diseases with Lewy bodies," Neurology, Jan. 2000, 54(2):407-411.
van der Staay et al., "The novel selective PDE9 inhibitor BAY 73-6691 improves learning and memory in rodents," Neuropharmacology, 2008, 55:908-918.
Wang et al., "Cyclic GMP-Dependent Protein Kinase and Cellular Signaling in the Nervous System," Journal of Neurochemistry, 1997, 68:443-456.
Winblad et al., "Ideal: A 6-month, double-blind, placebo-controlled study of the first skin patch for Alzheimer disease," Neurology, 2007,69(Suppl. 1):69:S14-S22.
Doose et al., "Single-Dose Pharmacokinetics and Effect of Food on the Bioavailability of Topiramate, A Novel Antiepileptic Drug," The Journal of Clinical Pharmacology, 1996, 36:884-891.
Notice of Allowance in U.S. Appl. No. 16/607,402, dated May 5, 2021, 8 pages.
Notice of Allowance in U.S. Appl. No. 16/607,402, dated Aug. 19, 2021, 10 pages.
Notice of Allowance in U.S. Appl. No. 16/607,402, dated Sep. 1, 2021, 7 pages.
Notice of Allowance in U.S. Appl. No. 16/607,459, dated May 18, 2021, 15 pages.
Notice of Allowance in U.S. Appl. No. 16/607,459, dated Jul. 30, 2021, 5 pages.
Notice of Allowance in U.S. Appl. No. 16/607,459, dated Aug. 19, 2021, 5 pages.
Notice of Allowance in U.S. Appl. No. 16/607,459, dated Sep. 10, 2021, 4 pages.
Office Action in Argentine Patent Application No. P120103702, dated Apr. 20, 2021, 11 pages (with English Translation).
Office Action in Australian Patent Application No. 2018278422, dated Jul. 7, 2021, 3 pages.
Office Action in Egyptian Patent Application No. PCT529/2014, dated Aug. 15, 2021, 12 pages (with English Translation).
Office Action in Indian Patent Application No. 201947044330, dated Jun. 14, 2021, 5 pages (with English Translation).
Office Action in Indian Patent Application No. 201947044352, dated Jun. 25, 2021, 6 pages (with English Translation).
Office Action in Indian Patent Application No. 201947044546, dated May 5, 2021, 5 pages (with English Translation).
Office Action in Indian Patent Application No. 201947044589, dated Jun. 29, 2021, 6 pages (with English Translation).
Office Action in Mexican Patent Application No. MX/a/2019/013 3 83, dated Aug. 17, 2021, 8 pages (with English Translation).
Office Action in Mexican Patent Application No. MX/a/2019/013 3 97, dated Aug. 31, 2021, 12 pages (with English Translation).
Office Action in Russian Patent Application No. 2019135261, dated Sep. 8, 2021, 15 pages (with English Translation).
Office Action in Russian Patent Application No. 2019135690, dated Aug. 25, 2021, 24 pages (with English Translation).
Office Action in U.S. Appl. No. 16/609,514, dated Jun. 8, 2021, 26 pages.

(56) References Cited

OTHER PUBLICATIONS

Submission Document in Argentine Patent Application No. P120103702, dated Jul. 5, 2021, 357 pages (with English Translation).
Submission Document in European Patent Application No. 18808870.2, dated Sep. 9, 2021, 9 pages.
Submission Document in European Patent Application No. 18809656.4, dated Aug. 19, 2021, 9 pages.
Submission Document in European Patent Application No. 18810202.4, dated Jun. 14, 2021, 23 pages.
Submission Document in European Patent Application No. 18810578.7, dated Aug. 16, 2021, 13 pages.
Submission Document in Mexican Patent Application No. MX/a/2019/013198, dated Jul. 21, 2021, 11 pages (with English Translation).
Submission Document in U.S. Appl. No. 16/607,402, dated Jul. 16, 2021, 15 pages.
Submission Document in U.S. Appl. No. 16/607,459, dated Aug. 13, 2021, 12 pages.
Submission Document in U.S. Appl. No. 16/607,459, dated Sep. 3, 2021, 13 pages.
Submission Document in U.S. Appl. No. 16/607,459, dated Sep. 16, 2021, 9 pages.
Notice of Allowance in U.S. Appl. No. 16/607,402, dated Oct. 8, 2021, 4 pages.
Office Action in European Patent Application No. 18810202.4, dated Nov. 15, 2021, 7 pages.
Submission Document in Egyptian Patent Application No. PCT529/2014, dated Nov. 3, 2021, 11 pages (with English Translation).
Office Action in Russian Patent Application No. 2019135838, dated Sep. 29, 2021, 10 pages (with English Translation).
Notice of Allowance in U.S. Appl. No. 16/607,402, dated Dec. 1, 2021, 4 pages.
Notice of Allowance in U.S. Appl. No. 16/607,402, dated Dec. 15, 2021, 4 pages.
Office Action in Mexican Patent Application No. MX/a/2019/013383, dated Jan. 12, 2022, 8 pages (with English Translation).
Office Action in Mexican Patent Application No. MX/a/2019/013397, dated Feb. 2, 2022, 15 pages (with English Translation).
Office Action in Taiwanese Patent Application No. 107118423, dated Dec. 23, 2021, 9 pages (with English Translation).
Submission Document in Mexican Patent Application No. MX/a/2019/013383, dated Dec. 15, 2021, 16 pages (with English Translation).
Submission Document in Mexican Patent Application No. MX/a/2019/013397, dated Jan. 13, 2022, 9 pages (with English Translation).
Submission Document in U.S. Appl. No. 16/607,402, dated Dec. 9, 2021, 13 pages.
Submission Document in U.S. Appl. No. 16/609,514, dated Dec. 7, 2021, 15 pages.
Submission Document in Australian Patent Application No. 2018278422, dated Feb. 21, 2022, 10 pages.

* cited by examiner

LEWY BODY DISEASE THERAPEUTIC AGENT CONTAINING PYRAZOLOQUINOLINE DERIVATIVE

TECHNICAL FIELD

The present invention relates to a therapeutic agent for dementia with Lewy bodies and Parkinson disease with dementia, comprising a pyrazoloquinoline derivative or a pharmaceutically acceptable salt thereof, which has an phosphodiesterase 9 (PDE9) inhibitory action on, as an active ingredient.

BACKGROUND ART

Dementia with Lewy bodies (DLB) and Parkinson disease (PD) are a progressive neurodegenerative disease in which an abnormal inclusion body primarily composed of α-synuclein (Lewy body) appears inside a neuron, leading to degeneration and loss of the neuron. Distribution of many Lewy bodies in the cerebral cortex leads to development of, for example, cognitive impairment, and distribution of many Lewy bodies in the brainstem leads to development of parkinsonism. In addition to these, psychiatric symptoms such as visual hallucinations, hallucinations, delusions, and depressive symptoms, sleep disorders, and autonomic symptoms are seen. When a person developed dementia before the onset of parkinsonism or within one year of the onset thereof, the person is diagnosed as dementia with Lewy bodies; and when parkinsonism was present for one or more years before the onset of dementia, the person is diagnosed as Parkinson disease with dementia (PDD). In this way, different diagnoses, which are dementia with Lewy bodies, Parkinson disease with dementia, and Parkinson disease, are given depending on, for example, the temporal order of appearance and difference in the extent of cognitive impairment and parkinsonism. However, these diseases are pathologically considered as the same disease and are collectively referred to as Lewy body disease (LBD). The characteristic of dementia with Lewy bodies is that, in brain SPECT or FDG PET, reduced blood flow and abnormal glucose metabolism, which are observed in the posterior cingulate gyrus and the parietotemporal association area in Alzheimer disease, are also observed in the occipital lobe including a visual area in addition to the posterior cingulate gyrus and the parietotemporal association. When dopamine transporter (DAT) imaging that assesses the function of an intracerebral dopamine nervous system is performed, reduced uptake of DAT in the striatum in a brain is observed in not only Parkinson disease but also dementia with Lewy bodies before the onset of parkinsonism (see Non Patent Literature 1). It is also reported that, in dementia with Lewy bodies and Parkinson disease, neurons of a basal nucleus of Meynert, which is a nucleus of origin of an acetylcholinergic nerve, are degenerated or lost, and a severe disorder of the acetylcholinergic nervous system is observed in the hippocampus, the cortex, and the like (see Non Patent Literatures 2, 3, and 4).

Currently there is no curative therapy that modifies the progress process itself of a brain lesion in dementia with Lewy bodies and Parkinson disease, and symptomatic treatment depending on symptoms has been administered. For a parkinsonian symptom, dopamine replacement therapy for example by taking L-DOPA, surgical therapy, and the like are used. For the cognitive impairment, only donepezil is approved for the indication of dementia with Lewy bodies and only rivastigmine is approved for the indication of Parkinson disease with dementia, and these are also effective against change of a cognitive function and a psychiatric symptom (hallucinations, delusions, apathy, depressive symptoms, or behavioral symptoms) (see Non Patent Literatures 5, 6, 7, and 8). However, there is a report that an acetylcholinesterase inhibitor aggravates the parkinsonian symptom (see Non Patent Literature 9), and currently there is no therapy that is available when the acetylcholinesterase inhibitor cannot be used from the viewpoint of a side effect and tolerability. Pimavanserin, which is a 5-HT$_{2A}$ inverse agonist, is approved as a therapeutic drug for the psychiatric symptom such as hallucinations and delusions experienced by a patient with Parkinson disease (see Non Patent Literature 10). However, as is the case with an atypical antipsychotic agent such as olanzapine, quetiapine, and risperidone, a black box warning indicates that mortality risk is increased when pimavanserin is used for treating the psychiatric symptom of dementia of elderly people. As described above, there is currently no fully satisfactory therapy for the cognitive impairment and the psychiatric symptom of dementia with Lewy bodies or Parkinson disease, and thus, development of an effective medicament has been long awaited.

An animal to which scopolamine or 6-OHDA (6-hydroxydopamine) was administered can be used as an animal model of cognitive impairment seen in Lewy body disease. Scopolamine is a muscarinic receptor inhibitor and blocks transduction of the acetylcholinergic nervous system. The acetylcholinergic nervous system is responsible for memory, attention, and the like, and a healthy subject or an animal to which scopolamine was administered develops a dementia-like amnestic symptom, which is alleviated by an medicament used for treating cognitive impairment of Lewy body disease (see Non Patent Literatures 11 and 12). 6-OHDA is a neurotoxin that selectively degenerates a dopaminergic nerve and a noradrenergic nerve. It is possible to make 6-OHDA act specifically on the dopaminergic nerve by using 6-OHDA with a selective noradrenaline reuptake inhibitor (e.g., desipramine). An animal to which 6-OHDA was administered develops cognitive impairment, which is alleviated by a medicament used for treating cognitive impairment of Lewy body disease (see Non Patent Literature 13).

A compound represented by formula (I) (referred to as Compound (I) hereinafter) or a pharmaceutically acceptable salt thereof exhibits a PDE9 inhibitory action and is expected to be efficacious against Alzheimer-type dementia (Patent Literature 1). There is a report stating that a PDE9 inhibitor exhibited the effect of improving cognitive function in a novel object recognition test using rats with scopolamine-induced cognitive impairment (see Non Patent Literature 14), but there is no known pyrazoloquinoline derivative that exhibited the effect of improving cognitive function.

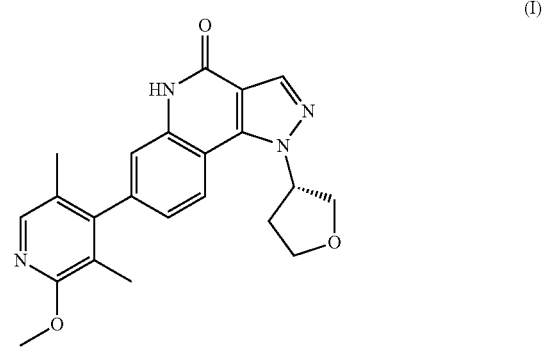 [SMILES: COc1ncc(C)c(-c2ccc3c(c2)[nH]c(=O)c2cnn([C@H]4CCOC4)c23)c1C]

(I)

CITATION LIST

Patent Literature

Patent Literature 1: U.S. Pat. No. 8,563,565

Non Patent Literature

Non Patent Literature 1: McKeith et al., Neurology, 65, pp. 1863-1872 2005
Non Patent Literature 2: Shimada et al., Neurology, vol. 73, pp. 273-278, 2009
Non Patent Literature 3: Tiraboschi et al., Neurology 54 (2000) 407-411
Non Patent Literature 4: Perry et. al., NeuroReport, vol. 5, pp. 747-749 (1994)
Non Patent Literature 5: Mori et al., Ann. Neurol, vol. 72, pp. 41-52 (2012)
Non Patent Literature 6: Dubois et al., Movement Disorders, vol. 27, pp. 1230-1238 (2012)
Non Patent Literature 7: Bergman et al., Clin. Neuropharmacol., vol. 25, pp. 107-110 (2002)
Non Patent Literature 8: McKeith, et al, Lancet, vol. 356, pp. 2031-2036 (2000)
Non Patent Literature 9: Bourke et al., Ann. Pharmacother. Vol. 32, pp. 610-611 (1998)
Non Patent Literature 10: Cummings et al., Lancet 2014, vol. 383, pp. 533-540
Non Patent Literature 11: Snyder et al., Alzheimer's & Dementia 1 (2005) 126-135
Non Patent Literature 12: Sambeth et al., European Journal of Pharmacology, vol. 572 (2007) pp. 151-159
Non Patent Literature 13: Kadowaki et al., Psychopharmacology (2013), 230, pp. 345-352
Non Patent Literature 14: Hutson et al., Neuropharmacology, 61 (2011) pp. 665-676

SUMMARY OF INVENTION

Technical Problem

It is an object of the present invention to provide a compound or a pharmaceutically acceptable salt thereof that exhibits an anti-dementia action in an animal model and has potential use as a therapeutic agent for Lewy body disease.

Solution to Problem

The present inventors conducted intensive research by using a rat model of scopolamine-induced cognitive impairment for achieving the above-mentioned object and consequently found that a pyrazoloquinoline derivative represented by formula (I) or a pharmaceutically acceptable salt thereof had the effect of suppressing cognitive impairment induced by scopolamine. The present inventors also found that the effect of improving cognitive function in Lewy body disease could be confirmed by assessment using a 6-OHDA model and completed the present invention.

Specifically, the present invention relates to the following <1> to <4>.
<1> A therapeutic agent for dementia with Lewy bodies or Parkinson disease with dementia, comprising (S)-7-(2-methoxy-3,5-dimethylpyridin-4-yl)-1-tetrahydrofuran-3-yl)-1H-pyrazolo[4,3-c]quinolin-4(5H)-one

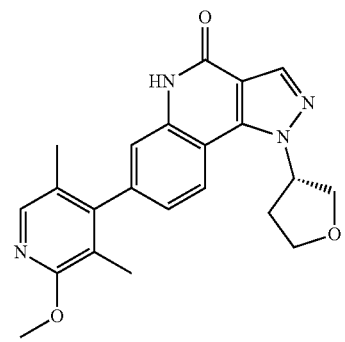

or a pharmaceutically acceptable salt thereof.
<2> A method for treating dementia with Lewy bodies or Parkinson disease with dementia, comprising administering (S)-7-(2-methoxy-3,5-dimethylpyridin-4-yl)-1-(tetrahydrofuran-3-yl)-1H-pyrazolo[4,3-c]quinolin-4(5H)-one

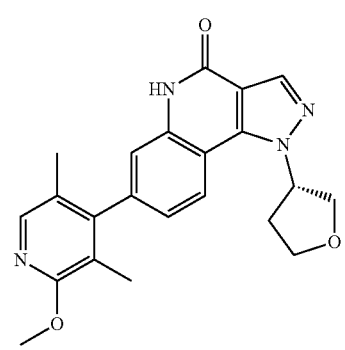

or a pharmaceutically acceptable salt thereof to a patient in need thereof.
<3> (S)-7-(2-Methoxy-3,5-dimethylpyridin-4-yl)-1-(tetrahydrofuran-3-yl)-1H-pyrazolo[4,3-c]quinolin-4(5H)-one

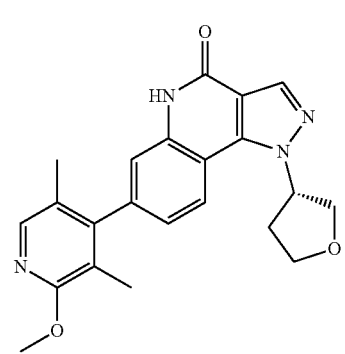

or a pharmaceutically acceptable salt thereof for use in treating dementia with Lewy bodies or Parkinson disease with dementia.
<4> Use of (S)-7-(2-methoxy-3,5-dimethylpyridin-4-yl)-1-(tetrahydrofuran-3-yl)-1H-pyrazolo[4,3-c]quinolin-4(5H)-one

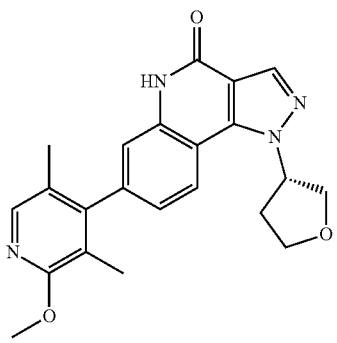

(I)

or a pharmaceutically acceptable salt thereof for the manufacture of a therapeutic agent for dementia with Lewy bodies or Parkinson disease with dementia.

Advantageous Effects of Invention

The pyrazoloquinoline derivative or a pharmaceutically acceptable salt thereof of the present invention exhibits the effect of suppressing cognitive impairment induced by scopolamine in the rat model of scopolamine-induced cognitive impairment, which is an animal model of Lewy body disease. Furthermore, the pyrazoloquinoline derivative or a pharmaceutically acceptable salt thereof of the present invention is expected to exhibit the effect of suppressing cognitive impairment in the 6-OHDA model, which is an animal model of Lewy body disease. Accordingly, the compound or a pharmaceutically acceptable salt thereof of the present invention has potential use as a therapeutic agent for Lewy body disease.

DESCRIPTION OF EMBODIMENTS

Hereinafter, the content of the present invention is described in detail.

"Pharmaceutically acceptable salt" as used herein is not particularly limited as long as the salt is a salt formed with the compound of the present invention and specific examples thereof include an acid addition salt such as a salt of an inorganic acid, a salt of an organic acid, and a salt of an acidic amino acid.

In the context of "pharmaceutically acceptable salt" as used herein, the number of acid molecules per one molecule of the above described compound in a formed salt is not particularly limited as long as the salt is formed at an appropriate ratio of the acid to the above described compound, unless specifically stated otherwise. In one embodiment, the number of acid molecules per one molecule of the above described compound is about 0.1 to about 5; in another embodiment, the number of acid molecules per one molecule of the above described compound is about 0.5 to about 2; and in still another embodiment, the number of acid molecules per one molecule of the above described compound is about 0.5, about 1, or about 2.

Specific examples of the salt of an inorganic acid include hydrochloride, hydrobromide, sulfate, nitrate, and phosphate; specific examples of the salt of an organic acid include acetate, succinate, fumarate, maleate, tartrate, citrate, lactate, stearate, benzoate, methanesulfonate, p-toluenesulfonate, and benzenesulfonate.

Specific examples of the salt of an acidic amino acid include aspartate and glutamate.

[Preparation]

The pharmaceutical composition of the present invention can be produced by mixing a pharmaceutically acceptable additive with Compound (I) or a pharmaceutically acceptable salt thereof. The pharmaceutical composition of the present invention can be produced in accordance with an already known method such as a method described in General Rules for Preparations of the Japanese Pharmacopoeia, 16th Edition.

The pharmaceutical composition of the present invention can be administered to a patient in an appropriate manner depending on the dosage form thereof.

The dosage of Compound (I) or a pharmaceutically acceptable salt thereof varies depending on the severity of the symptom, the age, the gender, the weight, the type of the dosage form and the salt, the specific type of the disease, and the like; and usually, in adults, about 30 µg to 10 g, in one embodiment 100 µg to 5 g, and in another embodiment 100 µg to 1 g is administered orally per day, in a single dose or in several divided doses; and about 30 µg to 1 g, in one embodiment 100 µg to 500 mg, and in another embodiment 100 µg to 300 mg is administered by injection per day, in a single dose or in several divided doses.

EXAMPLES

Compound (I) can be produced for example by the method described in Patent Literature 1.

Pharmacological Test Examples

The present inventors performed or can perform the following tests to confirm the effect of improving cognitive function in Lewy body disease.

[Test Example 1] Novel Object Recognition Test Using Rat with Scopolamine-Induced Cognitive Impairment A novel object recognition test using rats with scopolamine-induced cognitive impairment was performed to confirm the effect of improving cognitive impairment induced by an acetylcholine nerve disorder. The novel object recognition test is a test system for assessing cognitive function based on the spontaneous behavioral characteristic of a rodent in which the rodent spends more time exploring a novel object than a familiar object. The test method described in Ennacer etc. Behavioural Brain Research, 31 (1988) pp. 47-51 was partially modified and performed.

Materials and Methods

Six-week-old male Long Evans rats (the Institute for Animal Reproduction) were subjected to the test. For two days before the test, a process for habituating the rat to the experimental procedure was performed once daily. In the habituation process, administration of a vehicle to the rat was performed, and subsequently, the rat was placed in an empty test apparatus (40 cm×30 cm×H 45 cm) and allowed to explore for 3 minutes, was transferred into a waiting chamber (13 cm×30 cm×H 45 cm) for about 1 minute, and then was returned into the empty test apparatus again and allowed to stay for 5 minutes.

On the day of the test, an acquisition trial (T1) was performed. Compound (I) was administered orally by using a solution of 0.5% methylcellulose in 0.01 M hydrochloric acid as a vehicle 2 hours before T1. Scopolamine (Wako Pure Chemical Industries, Ltd.) was administered subcutaneously by using a saline as a vehicle at a dose of 0.7 mg/kg 30 minutes before T1. In T1, the rat was habituated to the empty test apparatus for 3 minutes, and then was transferred into the waiting chamber. After two identical objects were placed in the test apparatus, the rat was returned into the test apparatus again and allowed to explore the two identical objects freely for 5 minutes. Then, the rat was returned into a home cage. Two hours later, a retention trial (T2) was performed. The rat was placed in the empty test apparatus for 3 minutes for habituation and then was transferred into the waiting chamber. After one of the objects used in T1 (a "familiar" object) and one object not used in T1 (a "novel" object) were placed in the test apparatus, the rat was returned into the test apparatus again and allowed to explore these objects freely for 3 minutes. The objects were wiped with a wet wipe impregnated with ethanol after each experiment so that a smell serving as a clue did not stay. The behaviors of the rat during T1 and T2 were recorded by a digital video camera and the total exploration time for each object was measured manually using a stopwatch. Exploratory behavior was defined as the behavior of a rat in which the rat brings its nose within 2 cm of an object and directs its nose toward the object.

In the novel object recognition test, a percentage of exploration of the novel object during T2 is considered as an amnesia index that reflects discrimination between the familiar object and the novel object. The percentage of exploration of the novel object was calculated in accordance with the following equation.

The percentage of exploration of the novel object $(\%)=N/(N+F)\times 100$

F: time spent in exploring the familiar object
N: time spent in exploring the novel object Rats whose total time spent in exploring the objects during T1 or T2 was 10 seconds or less or rats whose percentage of the time spent in exploring either of the objects during T1 was not less than 70% or not more than 30% of the total exploration time were excluded from data analysis.

The results were expressed as mean±standard error. The difference between a normal control group untreated with scopolamine and a disease control group treated with scopolamine was analyzed by an unpaired t-test (significantly different: *). The difference between the disease control group and a group treated with a single medicament was analyzed using Dunnett's multiple comparison test (significantly different: #). $p<0.05$ was judged to be a statistically significant difference. Statistical analysis was performed by using GraphPad Prism version 5.04 or 6.02.

Results

In T2, rats in the disease control group showed a significant decrease in the percentage of exploration of the novel object compared with rats in the normal control group. This means that memory impairment was induced in the rats by scopolamine. Compound (I) exhibited a significant effect of improving the percentage of exploration of the novel object at 3.3 mg/kg and 10 mg/kg.

TABLE 1

| Scopolamine-administered group | | | |
|---|---|---|---|
| Normal control group | Disease control group | Compound (I) 3.3 mg/kg | Compound (I) 10 mg/kg |
| 73.8 ± 3.0 | 53.3 ± 2.2* | 68.5 ± 2.0# | 68.5 ± 1.6# |

[Test Example 2] Novel Object Recognition Test and Object Location Recognition Test Using 6-OHDA Model Examples of a preclinical disease model of Lewy body disease include a cell model or an animal model produced by modifying a Lewy body disease-related gene or introducing a Lewy body disease-related substance (for example, α-synuclein transgenic, overexpression of α-synuclein by using an AAV vector, Parkin knockout, DJ-1 knockout, and a model injected with an α-synuclein aggregate); an agent-administered model reflecting the disorder of nervous system identified in a patient with Lewy body disease (for example, a model administered with a neurotoxin such as 6-OHDA, MPTP, paraquat, rotenone, LPS, and a saporin toxin, and a model administered with a neuroleptic drug such as scopolamine); a neuron model derived from iPS cells of a patient. The effect of a medicament on Lewy body disease can be confirmed by using these preclinical disease models.

Herein, it is shown that the therapeutic effect on Lewy body disease can be confirmed by using the 6-OHDA model.

Male SD rats are used to produce the 6-OHDA model. The rat is secured in a brain stereotaxic apparatus under anesthesia, and a cannula is inserted into the brain after exposing the skull. 6-OHDA HDA dissolved in a saline containing ascorbic acid is injected by a microinjection pump over several minutes. Desipramine is administered before the injection of 6-OHDA to protect a noradrenergic nerve. A rat untreated with 6-OHDA is produced by inserting a cannula into the same site in the brain. Several days after the operation, a novel object recognition test or an object location recognition test is performed. The novel object recognition test is performed by using the test method described in Ennacer etc. Behavioural Brain Research, 31 (1988) pp. 47-51, with some modifications. The object location recognition test is performed by using the test method described in Dix Behavioural Brain Research 99 (1999) pp. 191-200, with some modifications. The object location recognition test is a test system for assessing cognitive function based on the spontaneous behavioral characteristic of a rodent in which exploratory behavior of the rodent increases when the environment surrounding an object is changed even though the object is a familiar object.

In both tests, a process for habituating the rodent to the experimental procedure is performed before the test day. In the habituating process, administration of a vehicle to the rat is performed, and the rat is allowed to explore freely in an empty test apparatus (40 cm×30 cm×H 45 cm) for a certain period of time (from several minutes to several tens of minutes).

On the day of the test, Compound (I) is administered orally before an acquisition trial (T1). In both tests, the rat is allowed to freely explore two identical objects placed in the test apparatus for a certain period of time (for several minutes) during T1. The rat is returned into a home cage, and then a retention trial (T2) is performed. In T2 of the novel object recognition test, one of the objects used in T1 (a "familiar" object) and one object not used in T1 (a "novel" object) are placed in the test apparatus, and the rat is allowed to explore these objects freely for a certain period of time (for several minutes). In T2 of the object location recognition test, one of the two identical objects presented in T1 is placed in the test apparatus at a novel location. The rat is allowed to explore these objects freely for a certain period of time (for several minutes). In both tests, the objects are wiped with a wet wipe impregnated with ethanol after each experiment so that a smell serving as a clue do not stay. The behaviors of the rat during T1 and 12 are recorded by a digital video camera and the total exploration time for each object is measured manually using a stopwatch. Exploratory behavior is defined as the behavior of a rat in which the rat brings its nose within 2 cm of an object and directs its nose toward the object.

In the novel object recognition test, a percentage of exploration of the novel object during T2 is considered as an amnesia index that reflects discrimination between the familiar object and the novel object. In the object location recognition test, a percentage of exploration of the novel location during T2 is considered as an amnesia index that reflects discrimination between the familiar location and the novel location. The percentage of exploration of the novel object and the percentage of exploration of the object at the novel location are calculated in accordance with the following equations.

The percentage of exploration of the novel object (%)=$N_O/(N_O+F_O)\times 100$ $F_O$: time spent in exploring the familiar object
$N_O$: time spent in exploring the novel object The percentage of exploration of the object at the novel location (%)=$N_l/(N_l+F_l)\times 100$ $F_l$: time spent in exploring the object at the familiar location
$N_l$: time spent in exploring the object at the novel location The percentage of exploration of the novel object or the percentage of exploration of the object at the novel location is compared between groups to confirm the effect of Compound (I).

The invention claimed is:
1. A method for treating dementia with Lewy bodies or Parkinson disease with dementia, comprising administering (S)-7-(2-methoxy-3,5-dimethylpyridin-4-yl)-1-(tetrahydrofuran-3-yl)-1H-pyrazolo[4,3-c]quinolin-4(5H)-one represented by formula (I)

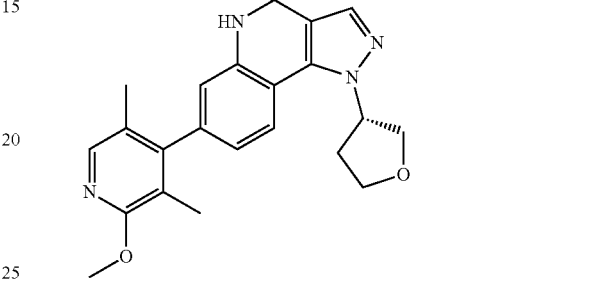

or a pharmaceutically acceptable salt thereof to a patient in need thereof.

* * * * *